(12) United States Patent
Ma

(10) Patent No.: US 10,975,050 B2
(45) Date of Patent: Apr. 13, 2021

(54) PROCESS FOR PREPARING OPTICALLY PURE (R)-4-N-PROPYL-DIHYDROFURAN-2(3H)-ONE

(71) Applicant: BEIJING ABLEPHARMTECH CO., LTD., Beijing (CN)

(72) Inventor: Liang Ma, Beijing (CN)

(73) Assignee: BEIJING ABLEPHARMTECH CO., LTD., Beijing (CN)

( * ) Notice: Subject to any disclaimer, the term of this patent is extended or adjusted under 35 U.S.C. 154(b) by 0 days.

(21) Appl. No.: 16/485,138

(22) PCT Filed: Apr. 23, 2017

(86) PCT No.: PCT/CN2017/081556
§ 371 (c)(1),
(2) Date: Aug. 9, 2019

(87) PCT Pub. No.: WO2018/152949
PCT Pub. Date: Aug. 30, 2018

(65) Prior Publication Data
US 2019/0359583 A1 Nov. 28, 2019

(30) Foreign Application Priority Data
Feb. 24, 2017 (CN) .......................... 201710102792.7

(51) Int. Cl.
*C07D 307/33* (2006.01)
*C07C 253/30* (2006.01)
*C07D 263/24* (2006.01)

(52) U.S. Cl.
CPC .......... *C07D 307/33* (2013.01); *C07C 253/30* (2013.01); *C07D 263/24* (2013.01)

(58) Field of Classification Search
CPC .. C07D 307/33; C07D 263/24; C07D 263/22; C07D 263/26; C07C 253/30; C07C 255/12
USPC ........................................................ 549/295
See application file for complete search history.

(56) References Cited

U.S. PATENT DOCUMENTS 4,696,943 A    9/1987   Gobert et al.

FOREIGN PATENT DOCUMENTS

| CN | 105646319 A | 6/2016 |
| CN | 105837535 A | 8/2016 |
| CN | 106008411 A | 10/2016 |
| EP | 0 162 036 A1 | 11/1985 |
| WO | 01/62726 A2 | 8/2001 |

OTHER PUBLICATIONS

Kenda, M.B., et al., "Discovery of 4-Substituted Pyrrolidone Butanamides as New Agents with Significant Antiepileptic Activity," Journal of Medicinal Chemistry, vol. 47, Issue 3, pp. 530-549 (2004).
Kosugi, H., et al., "Highly Enantiospecific Synthesis of 4-Alkyl and 4, 5-Dialkyl Substituted 4, 5-Dihydrofuran-2(3H)-ones from Optically Active (€)- and (2)-Alk-1-enyl p-Tolyl Sulphoxides: Application to the Synthesis of Lignan Lactones," Journal of the Chemical Society, Perkin Transactions I, pp. 935-943 (1989).
Mukaiyama, T., et al., "Asymmetric Synthesis of β-Substituted y Butyrolactones," Chemistry Letters, pp. 635-638 (1980).
Koch, C.S., and Chamberlin, A.R., "Enantioselective Preparation of 8 Alkyl-y-butyrolactones from Functionalized Ketene Dithioacetals," The Journal of Organic Chemistry, vol. 58, pp. 2725-2737 (1993).
"Ceder, O., and Nilsson, H.G., ""Synthesis of Optically Active Alcohols from3-Cyclohexene-1-carhoxylic Acid,"" Acta Chemica Scandinavica B, Organic Chemistry and Biochemistry, vol. 31, pp. 189-192 (1977)".
Schule, A., et al., "A Biocatalytic Route to the Novel Antiepileptic Drug Brivaracetam," Organic Process Research & Development, vol. 20, pp. 1566-1575 (2016).
CN First Search dated Mar. 27, 2019 as received in Application No. 201710102792.7.
CN First Office Action dated Apr. 2, 2019 as received in Application No. 201710102792.7.

*Primary Examiner* — Taylor V Oh
(74) *Attorney, Agent, or Firm* — Maschoff Brennan

(57) ABSTRACT

The present invention discloses a process for preparing optically pure (R)-4-n-propyl-dihydrofuran-2(3H)-one, belonging to the field of chemical synthesis. According to the process, optically pure (S)-3-n-pentanoyl-4-substituted oxazol-2-one is used as a starting material, and after alkylation, reduction, cyano hydrolysis, lactonization, the product optically pure (R)-4-n-propyl-dihydrofuran-2(3H)-one is given. The preparation process has the advantages of easy availability of raw materials, low price, high yield, high optical purity of product, simple reaction conditions and simple operations.

21 Claims, No Drawings

PROCESS FOR PREPARING OPTICALLY PURE (R)-4-N-PROPYL-DIHYDROFURAN-2(3H)-ONE

TECHNICAL FIELD

The present invention relates to a process for preparing optically pure (R)-4-n-propyl-dihydrofuran-2(3H)-one.

BACKGROUND ART

The preparation method of the 2-oxo-pyrrolidin-1-yl and its application as a medicament are described in the international patent application (publication No.: WO01/62726), which is particularly suitable for the treatment of neurological disorders. In particular, (2S)-2-((4R)-2-oxo-4-n-propyl-1-pyrrolidinyl) butanamide (also known as brivaracetam) is disclosed as a protective agent for the treatment and prevention of hypoxia and ischemic damage of central nervous system in the European Patent No. EP0162036, and the brivaracetam preparation made thereof has been approved by the European Medicines Agency (EMA) as an adjuvant therapy for partial epileptic seizure in patients over 16 years of age.

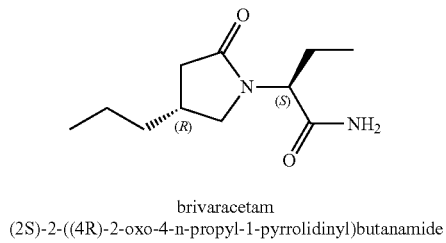

brivaracetam
(2S)-2-((4R)-2-oxo-4-n-propyl-1-pyrrolidinyl)butanamide

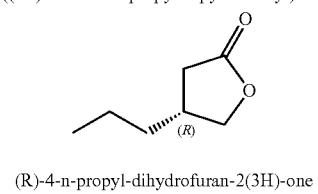

(R)-4-n-propyl-dihydrofuran-2(3H)-one

Benoit M. Kenda et al. (*J. Med. Chem.* 2004, 47, 530-549.) describe a method for preparing 2-oxo-pyrrolidin-1-yl using racemic 4-n-propyl-dihydrofuran-2(3H)-one. The product prepared by the racemic 4-n-propyl-dihydrofuran-2(3H)-one is a pair of diastereomers. As the isomers are similar in nature to the principal components and are difficult to remove by conventional recrystallization method, qualified products can be obtained by chiral column separation method. Chinese patent CN105646319 reported a process for preparing optically pure (R)-4-n-propyl-dihydrofuran-2(3H)-one and the preparation of brivaracetam therefrom. Due to the use of optically pure (R)-4-n-propyl-dihydrofuran-2(3H)-one, the obtained product has high chiral purity, therefore, brivaracetam with high optical purity can be obtained without chiral separation.

At present, seven synthetic routes for the preparation of optically pure (R)-4-n-propyl-dihydrofuran-2(3H)-one have been reported in relevant literatures.

Kosugi, H et al. (*J. Chem. Soc. Perkin Trans. I*. 1989, 935-943.) reported a synthetic route for optically pure (R)-4-n-propyl-dihydrofuran-2(3H)-one. According to the route, chiral sulfoxide is used as a starting material, after catalytic reduction by metal rhodium, cis olefin is obtained, and then it has a ring-closing reaction with trichloroacetic chloride under the catalysis of zinc powder, and then dechlorinated and desulfurized to obtain the product. However, in this route, the starting material is not readily available, and a precious metal ruthenium catalyst and a highly toxic metal tin catalyst are used, so it is not suitable for industrial production. The specific route is as follows:

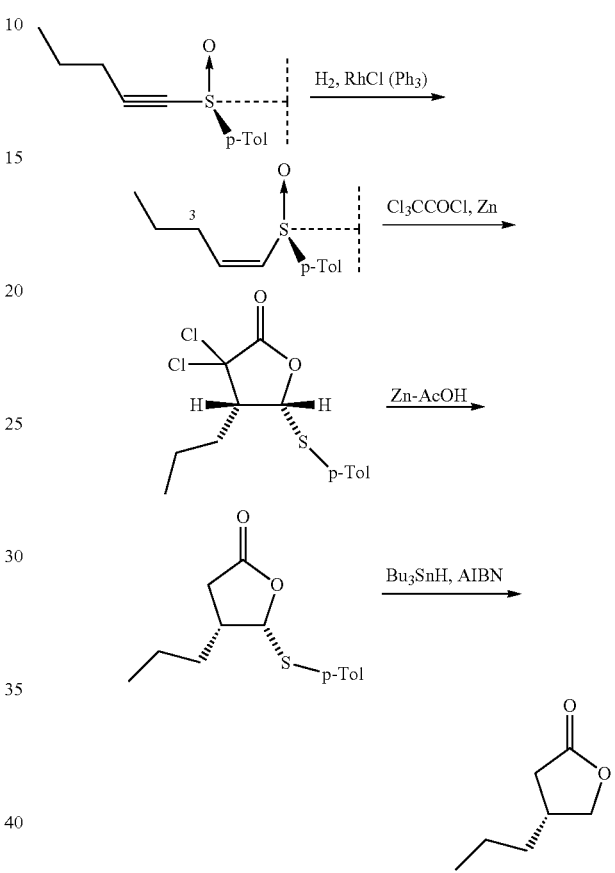

Mukaiyama, T et al. (*Chemistry Letters*. 1980, 635-638.) reported a synthetic route for optically pure (R)-4-n-propyl-dihydrofuran-2(3H)-one. According to the route, a chiral seven-membered ring is used as a starting material, and after addition, methylation, elimination and hydrolysis reactions, a chiral lactone is obtained. In this route, a complex intermediate is used as a starting material, which is not readily available and produces many byproducts, with poor atom economy, therefore, it is not suitable for industrial production. The specific route is as follows:

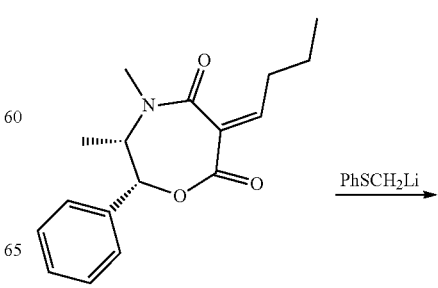

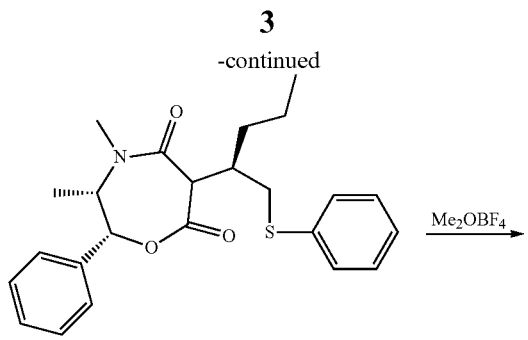
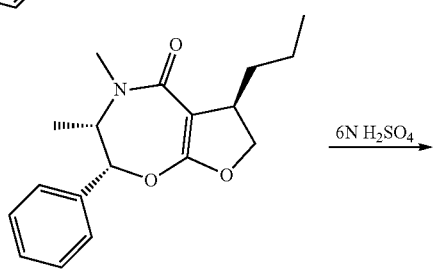

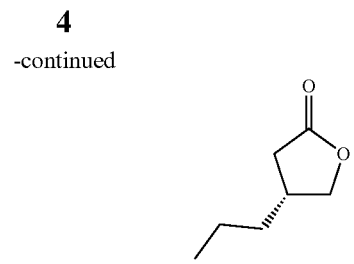

Chamberlin, R et al. (*J.O.C.* 1993, 58, 2725-2737.) reported a synthetic route for optically pure (R)-4-n-propyl-dihydrofuran-2(3H)-one. According to the route, double-substituted chiral oxazolinone and bromoacetyl chloride are used as starting materials, and after seven-step reactions, a chiral lactone is obtained, and a highly toxic mercury reagent is used in the last step. The synthetic route is long and has serious environmental pollution. Therefore, it is not suitable for industrial production. The specific route is as follows:

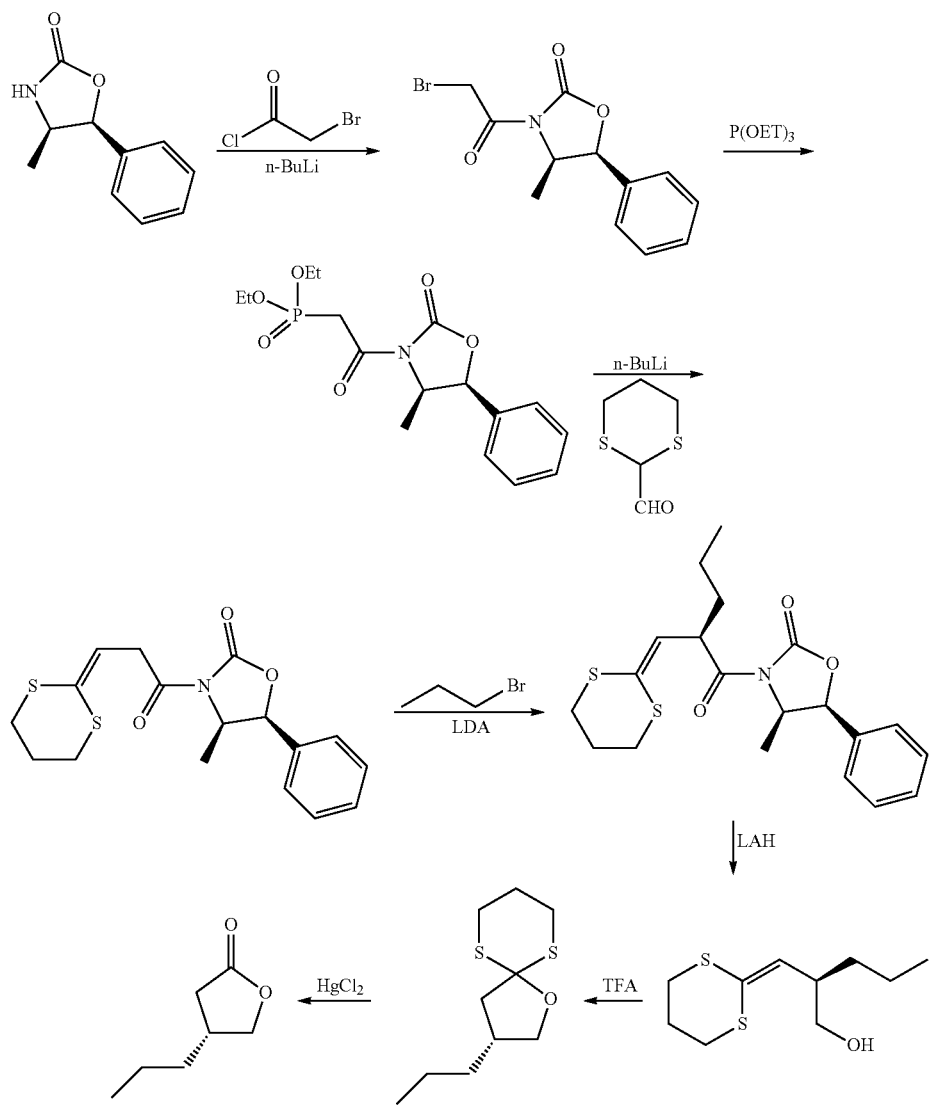

Olof Ceder et al. (*Acta Chemica Scandinavica, Series B: Organic Chemistry and Biochemistry.* 1977, 31, 189-192.) reported a synthetic route for optically pure (R)-4-n-propyl-dihydrofuran-2(3H)-one. According to the route, a chiral substituted cyclohexenoic acid is used as a starting material, and after reduction, oxidation and electrolysis reactions, a chiral lactone is prepared. In this route, a chiral intermediate that is not easily commercially available is used as a starting material and the product is obtained by electrolytic reaction. This route requires high cost and its reaction conditions are not suitable for mass production. The specific route is as follows:

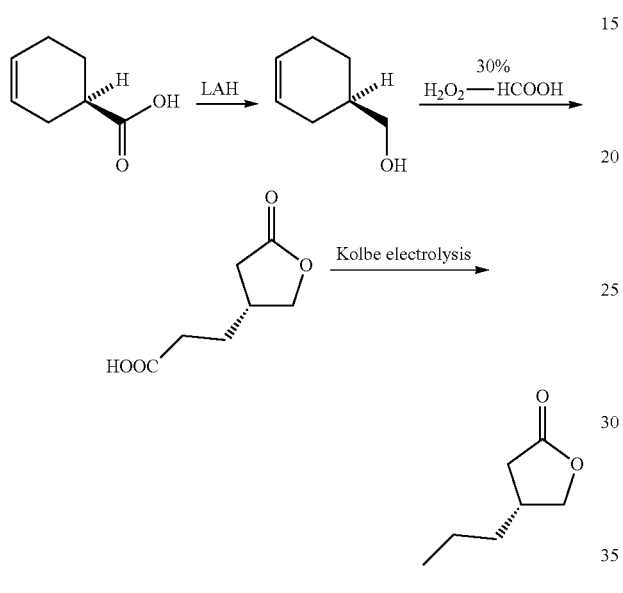

The Chinese patent CN105646319 reported a route for the preparation of optically pure (R)-4-n-propyl-dihydrofuran-2(3H)-one. According to the route, diphenyl malonate and (R)-epichlorohydrin are used as starting materials, and a chiral lactone is obtained by ring-closing, Grignard reaction and decarboxylation. Although the starting materials are readily available in this route, the third step of the decarboxylation reaction needs to be carried out above 130° C. with a long time, and the product may be racemized under prolonged heating conditions, affecting the product purity. The specific route is as follows:

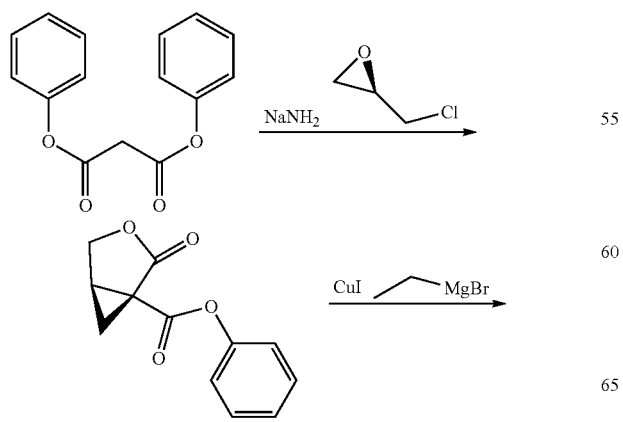

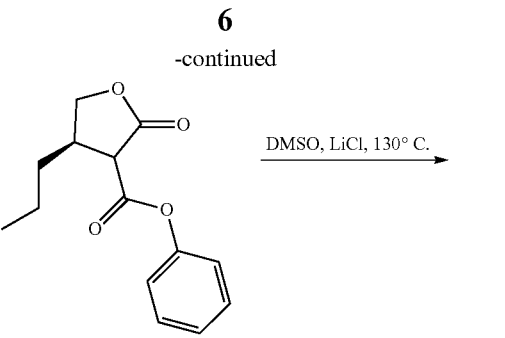

Chinese Patent CN105837535 reported a route for the preparation of optically pure (R)-4-n-propyl-dihydrofuran-2(3H)-one. According to the route, valeryl chloride, chiral oxazolinone and tert-butyl 2-bromoacetate are used as starting materials, and after condensation, substitution, reduction and hydrolysis reactions, a chiral lactone is obtained. In this route, the intermediates are purified by column chromatography, which is costly and cumbersome to operate. The specific route is as follows:

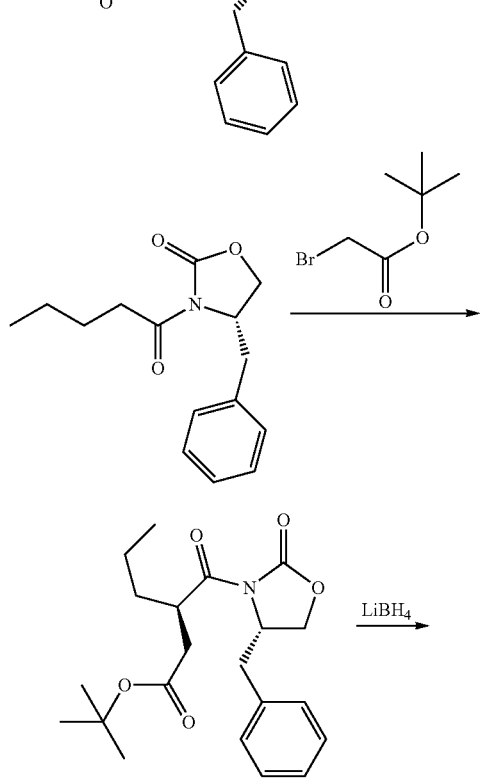

-continued

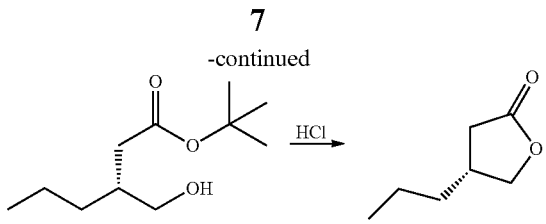

Arnaud Schülé et al. (*Org. Process Res. Dev.* 2016, 20, 1566-1575.) reported a route for the preparation of optically pure (R)-4-n-propyl-dihydrofuran-2(3H)-one. According to the route, a racemic substituted malonate is used as a starting material, after enzymatic resolution, a (R) isomer is obtained, followed by reduction and ring-closing reactions, a chiral lactone is obtained. This route is costly due to stringent reaction conditions for enzymatic catalysis. The specific route is as follows:

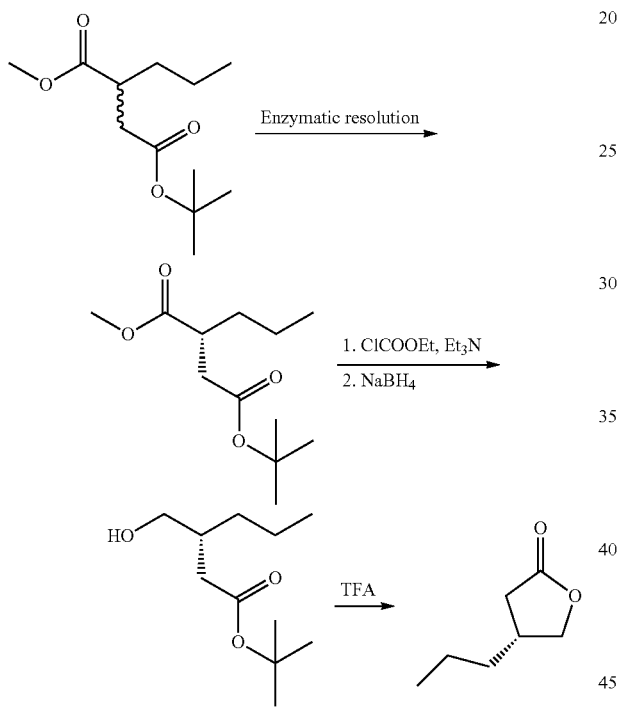

In order to overcome the problems in the reported routes, inventors have devised a new process of preparing optically pure (R)-4-n-propyl-dihydrofuran-2(3H)-one, and verified its feasibility by experiments. For the new technological route, the starting materials are readily available, the reaction yield is high, the by-products in the reaction can be recycled, the operations are simple and the enantioselectivity is good, so it has a broad industrial application prospect.

SUMMARY OF THE INVENTION

The present invention provides a simple and economical process for preparing optically pure (R)-4-n-propyl-dihydrofuran-2(3H)-one (formula I).

A process for preparing optically pure (R)-4-n-propyl-dihydrofuran-2(3H)-one, comprising the following steps:
1) preparing an optically pure (R)-3-(hydroxymethyl)hexanenitrile compound of formula (V);
2) conducting cyano hydrolysis and lactonization of (R)-3-(hydroxymethyl)hexanenitrile compound of formula (V) under acidic conditions to obtain optically pure (R)-4-n-propyl-dihydrofuran-2(3H)-one of formula I, or conducting cyano hydrolysis, acidification and lactonization under alkaline conditions to obtain optically pure (R)-4-n-propyl-dihydrofuran-2(3H)-one of formula I;

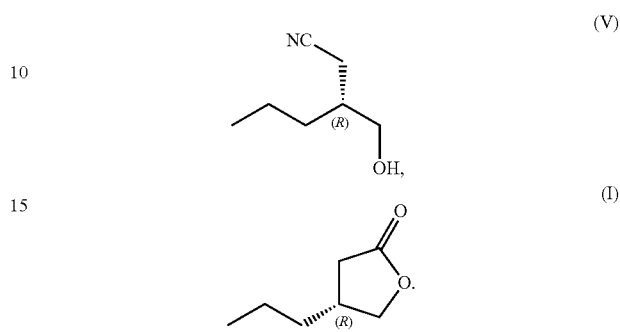

The acid used for cyano hydrolysis or/and lactonization is an organic acid or an inorganic acid, and the organic acid is p-toluenesulfonic acid, trifluoroacetic acid, formic acid, acetic acid or propionic acid; the inorganic acid is hydrochloric acid, sulfuric acid, nitric acid or phosphoric acid.

The acid used for cyano hydrolysis or/and lactonization is preferably hydrochloric acid or sulfuric acid.

The base used for cyano hydrolysis is sodium hydroxide, potassium hydroxide, lithium hydroxide, potassium carbonate or sodium carbonate.

The base used for cyano hydrolysis is preferably sodium hydroxide.

The reaction temperature of cyano hydrolysis is 0~100° C.

For the method for preparing a compound of formula (V) in step (1), a compound of the formula (IV) is used to prepare an optically pure (R)-3-(hydroxymethyl)hexanenitrile compound of formula (V) in the presence of a reducing agent, and (S)-4-substituted oxazol-2-one of the formula VI as a prosthetic group is recycled.

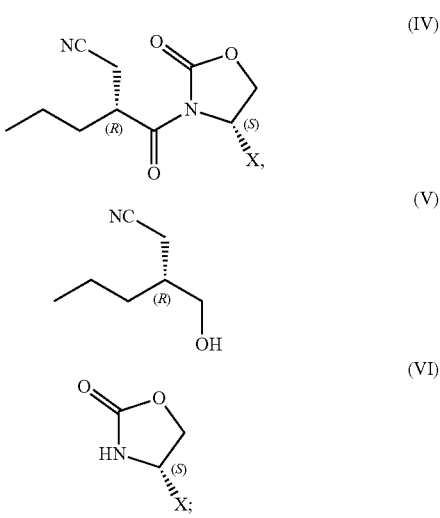

X is a substituted or unsubstituted $C_{1-20}$ alkyl, $C_{1-20}$ alkenyl, aryl, heteroaryl, heterocycloalkyl, arylalkyl or heteroarylalkyl.

9

Preferably:

X is a $C_{1-6}$ alkyl, substituted $C_{1-6}$ alkyl, $C_{2-6}$ alkenyl, aryl, heteroaryl, substituted aryl, arylalkyl or substituted arylalkyl.

X is a $C_{1-6}$ alkyl, aryl, substituted aryl, arylalkyl or substituted arylalkyl.

X is preferably methyl, ethyl, n-propyl, isopropyl, tert-butyl, benzyl, substituted benzyl, phenyl or substituted phenyl.

X is phenyl, isopropyl or benzyl.

The reducing agent is lithium borohydride, sodium borohydride, potassium borohydride, L-selectride or K-selectride.

The molar ratio of the compound of formula (IV) to the reducing agent is 1:0.5-5.

The reaction solvent for the reduction of the compound of formula (IV) is a single solvent of water, tetrahydrofuran, methanol, ethanol, isopropanol or a mixed solvent with water, and the reaction temperature is 0 to 100° C.

The method for preparing the compound of formula (IV) comprises the following steps:

A) providing the compound of optically pure (S)-3-n-pentanoyl-4-substituted oxazol-2-one of formula (II), B) carrying out an alkyl group substitution reaction between the compound of formula (II) and substituted acetonitrile of formula (III) in the presence of an alkaline reagent to generate a compound of formula (IV),

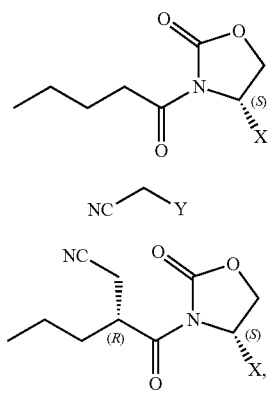

Where,

Y is selected from the group consisting of a halogen, a sulfonate group, —S$^+$Me$_2$ or —N$_2$$^+$ leaving group.

The base used for the alkylation is lithium diisopropylamide (LDA), lithium hexamethyldisilazide (LHMDS), potassium hexamethyldisilazide (KHMDS), sodium hexamethyldisilazide (NHMDS).

In the step B), the molar ratio of the compound of formula (II) to the compound of formula (III) is 1:0.9-5, and the molar ratio of the compound of formula (II) to the base is 1:0.9-3.

The reaction solvent for alkylation is tetrahydrofuran or 2-methyltetrahydrofuran, and the reaction temperature for alkylation is 20 to −80° C.

10

The Y is fluorine, chlorine, bromine, iodine, methanesulfonyloxy, trifluoromethanesulfonyloxy or p-toluenesulfonyloxy.

Preferably, Y is bromine, fluorine or chlorine.

The compound of formula (II) is prepared by reacting the compound of the formula (VI) with n-valeric acid or n-pentanoyl chloride or a mixed anhydride of n-valeric acid.

In the present invention, the optically pure (R)-3-(hydroxymethyl)hexanenitrile is subjected to cyano hydrolysis reaction under acidic or alkali conditions, and then lactonization under acidic conditions to obtain the target product of the present invention. Moreover, during the reaction process, the configuration of chiral center is not changed. The overall reaction process is as follows:

Step (1): conducting an alkyl substitution reaction between optically pure (S)-3-n-pentanoyl-4-substituted oxazol-2-one of the formula (II) and substituted acetonitrile of the formula (III) in the presence of an alkaline reagent, to generate a compound of formula (IV).

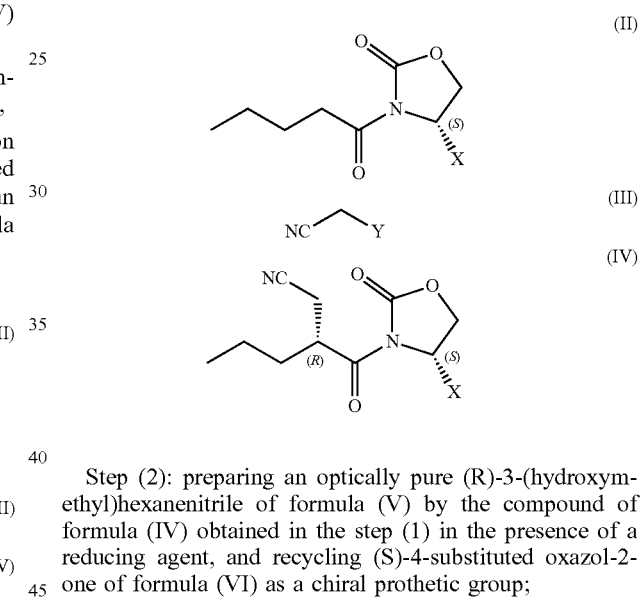

Step (2): preparing an optically pure (R)-3-(hydroxymethyl)hexanenitrile of formula (V) by the compound of formula (IV) obtained in the step (1) in the presence of a reducing agent, and recycling (S)-4-substituted oxazol-2-one of formula (VI) as a chiral prothetic group;

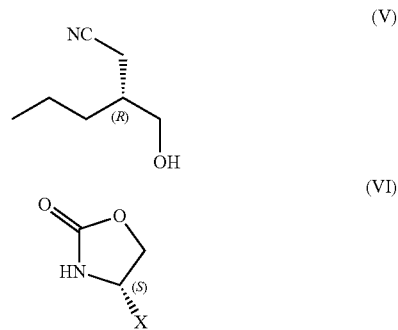

Step (3): conducting a cyano hydrolysis and lactonization of the optically pure (R)-3-(hydroxymethyl)hexanenitrile obtained in the step (2) under acidic condition, or conducting cyano hydrolysis under alkaline conditions and conducting acidification to prepare optically pure (R)-4-n-propyl-dihydrofuran-2(3H)-one.

The entire synthetic route is as follows:

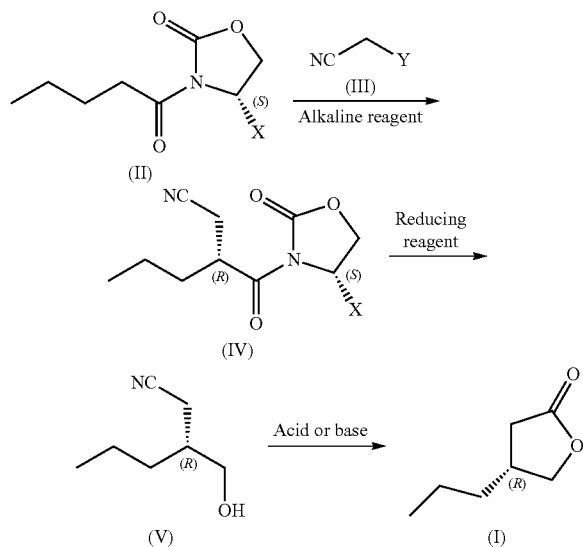

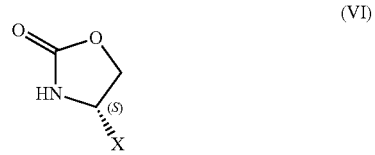

The term "alkyl" as used herein refers to a saturated monovalent hydrocarbon group having a linear, branched or cyclic chain moiety or a combination thereof and having 1 to 20 carbon atoms. The acyclic alkyl group preferably has 1 to 6 carbon atoms and the cyclic alkyl group preferably has 3 to 8 carbon atoms.

The term "alkenyl" as used herein refers to an unsubstituted or substituted branched, unbranched or cyclic hydrocarbon group having at least one double bond or a combination thereof. The "alkenyl" moiety can be optionally substituted with 1 to 5 substituents independently selected from halo, hydroxy, alkoxy, ester, acyl, cyano, acyloxy, carboxylic acid, amide or amino.

The term "aryl" as used herein includes a group derived from the removal of one hydrogen atom from an aryl hydrocarbon, such as a phenyl or a naphthyl.

The term "heterocycloalkyl" as used herein denotes a cyclic alkyl (cycloalkyl) group containing at least one O, S and/or N atom-interrupted carbocyclic structure, such as tetrahydrofuranyl, tetrahydropyranyl, piperidinyl, piperazinyl, morpholino and pyrrolidinyl.

The term "heteroaryl" as used herein denotes an "aryl" group as defined above containing at least one O, S and/or N atom-interrupted carbocyclic structure, such as pyridinyl, furyl, pyrrolyl, thienyl, isothiazolyl, imidazolyl, benzimidazolyl, tetrazolyl, pyrazinyl, pyrimidinyl, quinolyl, isoquinolinyl, isobenzofuranyl, benzothiophenyl, pyrazolyl, indolyl, isoindolyl, purinyl, carbazolyl, isoxazolyl, thiazolyl, oxazolyl, benzothiazolyl or benzooxazolyl.

The term "halogen" as used herein includes chlorine, bromine, iodine and fluorine.

The term "cyano" as used herein represents a group of the formula —CN.

The term "hydroxyl" as used herein represents a group of the formula —OH.

The compound of formula (II) as used herein can be prepared by any suitable method.

The (S)-3-n-pentanoyl-4-substituted oxazol-2-one of the formula (II) is preferably produced by reacting optically pure (S)-4-substituted oxazol-2-one with n-valeric acid or n-pentanoyl chloride or a mixed anhydride of n-valeric acid.

In the process of the present invention, the base used in the alkylation reaction of the step (1) is selected from lithium diisopropylamide (LDA), lithium hexamethyldisilazide (LHMDS), potassium hexamethyldisilazide. (KHMDS), sodium hexamethyldisilazide (NHMDS); preferably selected from lithium hexamethyldisilazide (LHMDS) or lithium diisopropylamide (LDA).

In the process of the present invention, for the compound of the formula (IV), when X is a benzyl group, the solvent for recrystallization is selected from the group consisting of a single solvent of methanol, ethanol, isopropanol, methyl tert-butyl ether, acetone, butanone, isopropyl ether or a mixed solvent of n-heptane/ethyl acetate, methanol/water, ethanol/water, isopropanol/water, acetonitrile/water; preferably ethanol, isopropanol.

Chiral oxazolinones (compounds of formula IV) are known as Evans prosthetic groups and are commonly used chiral prosthetic groups. After N-acylation of a prosthetic group, if an alkyl side chain is introduced at the position a of the side chain amide, the selectivity of the newly formed chiral center can be controlled. The reaction mechanism is that a base, for example lithium diisopropylamide, and a substrate form an enol form under a low temperature condition, and then reaction with a halogenated alkane is conducted. The reaction has good enantioselectivity, and the obtained product has high optical purity.

The applicant has discovered that, in the new route of the present invention, a compound of formula II and a compound of formula III are used to prepare a novel compound of formula IV. When reaction at a low temperature, the chiral center contained in the compound of formula II can induce the construction of a new chiral center stereospecifically, and no diastereomers are observed, with very good stereoselectivity of reaction. There are a small amount of diastereomers formed during the reaction and these diastereomers can be removed by a simple recrystallization process. In addition, the reaction does not produce structurally similar by-products, with a high conversion rate. Therefore, it can solve the problems of poor reaction selectivity and low yield in the prior art to a greatest extent.

In the process of the present invention, the reducing agent used in the reduction reaction of the step (2) is selected from the group consisting of lithium aluminum hydride, lithium borohydride, sodium borohydride, potassium borohydride, lithium aluminum tri-tert-butoxide, L-selectride, K-selectride; preferably selected from sodium borohydride, potassium borohydride, lithium borohydride; most preferably selected from sodium borohydride, potassium borohydride.

The applicant has discovered that, in the new route of the present invention, a compound of the formula IV is used to prepare a novel compound of the formula V and the chemical selectivity of the reaction is very good, and the reduction site is only in the amide bond of oxazolinone. No by-product of the reduction of the cyano group is observed; in addition, after reaction, the compound of the formula VI can be recycled by recrystallization, which greatly improves the atom economy and reduces the cost.

In the process of the present invention, the alkaline reagent used for the cyano hydrolysis reaction of step (3) is selected from sodium hydroxide, potassium hydroxide, lithium hydroxide, potassium carbonate or sodium carbonate; preferably selected from sodium hydroxide, potassium hydroxide; and most preferably selected from sodium hydroxide.

In the process of the present invention, the acid used for lactonization reaction is selected from an organic acid such as p-toluenesulfonic acid, trifluoroacetic acid, formic acid, acetic acid, propionic acid; or an inorganic acid such as hydrochloric acid, sulfuric acid, and nitric acid, phosphoric acid; and most preferably selected from hydrochloric acid.

In the process of the present invention, when cyano hydrolysis and lactonization occur simultaneously under an acidic condition in the step (3), the acid used is selected from the group consisting of inorganic acids, such as hydrochloric acid, sulfuric acid, nitric acid, phosphoric acid; and most preferably selected from sulfuric acid or hydrochloric acid.

In the process of the present invention, the molar ratio of the compound of formula (II) to the compound of formula (III) in the step (1) is 1:0.9-5, preferably 1:1.1-1.5.

In the process of the present invention, the molar ratio of compound of formula (II) to the base in the step (1) is 1:0.9-3, preferably 1:1.0-1.5.

In the process of the present invention, the molar ratio of compound of formula (IV) to the reducing agent in the step (2) is 1:0.5-5, preferably 1:1.0-2.0.

In the process of the present invention, the reaction solvent for alkylation in the step (1) is tetrahydrofuran, 2-methyltetrahydrofuran.

In the process of the present invention, the reaction solvent for the reduction in the step (2) is a mixed solvent of water/tetrahydrofuran, water/methanol, and water/ethanol.

In the process of the present invention, the reaction solvent for cyano hydrolysis in the step (3) is water or a mixed solvent with tetrahydrofuran.

In the process of the present invention, the reaction temperature for alkylation in the step (1) is 20 to −80° C.

In the process of the present invention, the reaction temperature for reduction in the step (2) is 0 to 100° C.

In the process of the present invention, the reaction temperature for acid hydrolysis of cyano group in the step (3) is 0 to 100° C., preferably 80 to 100° C.

In the process of the present invention, the reaction temperature for basic hydrolysis of cyano group in the step (3) is 0 to 100° C., preferably 70 to 90° C.

Optically pure (R)-4-propyldihydrofuran-2(3H)-one can be prepared by the process of the present invention.

The process of the present invention is particularly suitable for the preparation of 4-n-propyl-dihydrofuran-2(3H)-one with the (R) configuration. The term (R) as used herein refers to a compound which has an enantiomeric composition of 50% or more, preferably 90% or more.

The following embodiments are merely illustrative of the present invention and are not to be construed as limiting the invention. Routine modifications and improvements can be made by those skilled in the art without departing from the spirit and scope of the present invention.

DETAILED DESCRIPTION OF THE PREFERRED EMBODIMENTS

Embodiment 1: Synthesis of (S)-4-benzyl-3-pentanoyloxazol-2-one

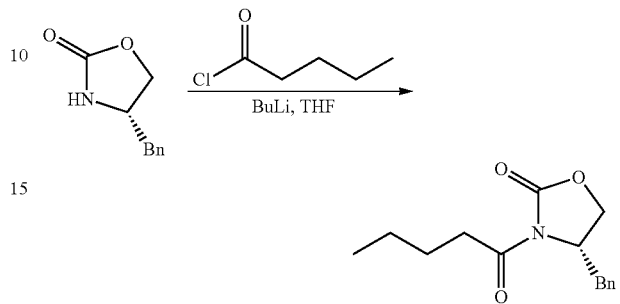

In a reaction flask, tetrahydrofuran (6.3 L) was added, (S)-4-benzyloxazol-2-one (422.0 g, 2.38 mol) was added, and the temperature was cooled to −70° C.; under nitrogen gas protection, the internal temperature was maintained at −65~−75° C., 2.5 M n-butyllithium (1.0 L, 2.5 mol, 1.05 eq) solution was added dropwise, after the addition, the reaction was conducted for half an hour at a maintained temperature; then the internal temperature was maintained at −65~−75° C., valeryl chloride (315.9 g, 2.62 mol, 1.1 eq) was added dropwise and reacted for 1 hour, and TLC was used to detect the disappearance of (S)-4-benzyloxazol-2-one, and treatment was performed; then the temperature was raised to 0° C., 2 L saturated aqueous ammonium chloride solution was added and quenched by butyl lithium to separate the phase. The organic phase was concentrated under a reduced pressure and concentrated to dryness. The concentrate was dissolved in 3 L methylene dichloride, washed with water twice (500 mL×2). The organic phase was dried over 300.0 g anhydrous sodium sulfate for 2 hours; filtered and concentrated under a reduced pressure to give the target product as a white solid (621.3 g, yield 99.9%).

$^1$H NMR (400 MHz, CDCl$_3$) δ 7.33 (t, J=7.2 Hz, 2H), 7.28 (d, J=7.3 Hz, 1H), 7.21 (d, J=7.2 Hz, 2H), 4.67 (ddd, J=10.6, 7.1, 3.6 Hz, 1H), 4.26-4.08 (m, 2H), 3.29 (dd, J=13.4, 3.1 Hz, 1H), 3.04-2.84 (m, 2H), 2.77 (dd, J=13.3, 9.6 Hz, 1H), 1.68 (ddd, J=16.9, 11.0, 6.1 Hz, 2H), 1.41 (dt, J=15.0, 7.7 Hz, 2H), 0.96 (t, J=7.4 Hz, 3H). MS (ESI): m/z 262.1 [M+H]$^+$. [α]$_D^{20}$ +54.0° (c=1.0 g/100 mL, CHCl$_3$).

Embodiment 2: (S)-4-phenyl-3-pentanoyloxazol-2-one

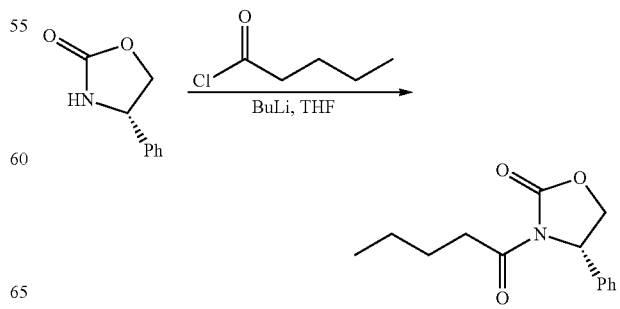

In a reaction flask, tetrahydrofuran (50 mL) was added, (S)-4-phenyloxazol-2-one (5.0 g, 30.6 mmol) was added, and the temperature was cooled to −70° C.; under nitrogen gas protection, the internal temperature was maintained at −65~−75° C., 2.5 M n-butyllithium (12.9 mL, 32.2 mmol, 1.05 eq) solution was added dropwise, after the addition, the reaction was conducted for half an hour at a maintained temperature; then the internal temperature was maintained at −65~−75° C., valeryl chloride (4.1 g, 34.0 mmol, 1.11 eq) was added dropwise and reacted for 1 hour, and TLC was used to detect the disappearance of (S)-4-phenyloxazol-2-one, and treatment was performed; then the temperature was raised to 0° C., 20 mL saturated aqueous ammonium chloride solution was added and quenched by butyl lithium to separate the phase. The organic phase was concentrated under a reduced pressure. The concentrate was dissolved in 50 mL methylene dichloride, washed with water twice (25 mL×2). The organic phase was dried over 10.0 g anhydrous sodium sulfate for 2 hours; filtered and concentrated under a reduced pressure to give the target product as a white solid (7.4 g, yield 97.6%).

$^1$H NMR (600 MHz, CDCl$_3$) δ 7.38 (dd, J=8.2, 6.6 Hz, 2H), 7.35-7.31 (m, 1H), 7.31-7.27 (m, 2H), 5.42 (dd, J=8.7, 3.7 Hz, 1H), 4.68 (t, J=8.8 Hz, 1H), 4.27 (dd, J=8.9, 3.7 Hz, 1H), 2.93 (td, J=7.4, 2.6 Hz, 2H), 1.63-1.53 (m, 3H), 1.33 (dtd, J=15.1, 7.6, 5.5 Hz, 2H), 0.89 (t, J=7.4 Hz, 3H). MS (ESI): m/z 248.1 [M+H]$^+$. [α]$_D^{19}$ +60.0° (c=1.0 g/100 mL, CHCl$_3$).

Embodiment 3:
(S)-4-isopropyl-3-pentanoyloxazol-2-one

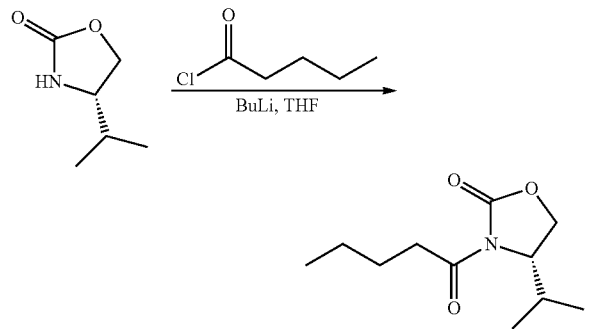

In a reaction flask, tetrahydrofuran (50 mL) was added, (S)-4-isopropyloxazol-2-one (5.0 g, 38.7 mmol) was added, and the temperature was cooled to −70° C.; under nitrogen gas protection, the internal temperature was maintained at −65~−75° C., 2.5 M n-butyllithium (16.2 mL, 40.5 mmol, 1.05 eq) solution was added dropwise, after the addition, the reaction was conducted for half an hour at a maintained temperature; then the internal temperature was maintained at −65~−75° C., valeryl chloride (5.1 g, 42.3 mmol, 1.09 eq) was added dropwise and reacted for 1 hour, and TLC was used to detect the disappearance of (S)-4-isopropyloxazol-2-one, and treatment was performed; then the temperature was raised to 0° C., 20 mL saturated aqueous ammonium chloride solution was added and quenched by butyl lithium to separate the phase. The organic phase was concentrated under a reduced pressure. The concentrate was dissolved in 50 mL methylene dichloride, washed with water twice (25 mL×2). The organic phase was dried over 10.0 g anhydrous sodium sulfate for 2 hours; filtered and concentrated under a reduced pressure to give the target product as a light yellow oily substance (8.0 g, yield 96.8%).

$^1$H NMR (600 MHz, CDCl$_3$) δ 4.44 (ddd, J=8.4, 3.9, 3.1 Hz, 1H), 4.26 (t, J=8.7 Hz, 1H), 4.20 (dd, J=9.1, 3.0 Hz, 1H), 2.99 (ddd, J=16.6, 8.7, 6.3 Hz, 1H), 2.86 (ddd, J=16.5, 8.6, 6.4 Hz, 1H), 2.37 (dtd, J=14.0, 7.0, 3.9 Hz, 1H), 1.69-1.58 (m, 3H), 1.39 (h, J=7.5 Hz, 2H), 0.96-0.90 (m, 7H), 0.88 (d, J=7.0 Hz, 3H). MS (ESI): m/z 214.1 [M+H]$^+$. [α]$_D^{19}$ +75.0° (c=1.0 g/100 mL, CHCl$_3$).

Embodiment 4: Synthesis of (R)-3-((S)-4-benzyl-2-oxooxazolidinyl-3-carbonyl)hexanenitrile Method I:

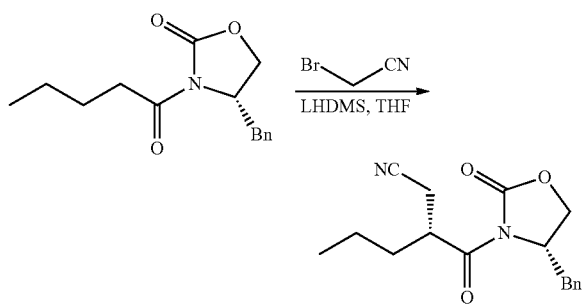

In a reaction flask, tetrahydrofuran (100.0 mL) was added, (S)-4-benzyl-3-pentanoyloxazol-2-one (10.0 g, 38.3 mmol, 1.0 eq) was added, and the temperature was cooled to −70° C.; under nitrogen gas protection, the internal temperature was maintained at −65~−75° C., 1.0 M solution of LHMDS in tetrahydrofuran (49.8 mL, 49.8 mmol, 1.3 eq) was added dropwise, after the addition, the reaction was conducted for 1 hour at a maintained temperature; then the internal temperature was maintained at −65~−75° C., bromoacetonitrile (6.9 g, 57.5 mmol, 1.5 eq) was added dropwise, and the reaction conducted for 1-2 hours at a maintained temperature. TLC was used to detect the disappearance of (S)-4-benzyl-3-pentanoyloxazol-2-one and treatment was performed; then the temperature was raised to 0° C., 200.0 mL saturated aqueous ammonium chloride solution was added to separate the phase. The organic phase was concentrated under a reduced pressure to dryness. The concentrate was dissolved in 100.00 mL methylene dichloride, washed with water twice (50.0 mL×2). The organic phase was dried over 30.0 g anhydrous sodium sulfate for 2 hours; filtered and concentrated under a reduced pressure to give 12.0 g crude product. Then 22.0 mL of ethanol was added to the crude product, heated to reflux, dissolved and crystallized after cooled, when cooled to 0~5°, stirred for 1 hour at a constant temperature, filtered and the filter cake was rinsed with a small amount of ethanol, after rinsed, the solid was dried in a vacuum oven for 4 hours to give the target product as a white solid (9.9 g, yield 86.1%).

$^1$H NMR (400 MHz, CDCl$_3$) δ 7.34 (t, J=7.1 Hz, 2H), 7.31-7.25 (m, 1H), 7.22 (d, J=7.0 Hz, 2H), 4.69 (qd, J=6.9, 3.5 Hz, 1H), 4.32-4.19 (m, 2H), 4.19-4.05 (m, 1H), 3.33 (dd, J=13.5, 3.0 Hz, 1H), 2.83 (dd, J=13.4, 9.6 Hz, 1H), 2.73 (dd, J=16.8, 7.8 Hz, 1H), 2.61 (dd, J=16.8, 5.5 Hz, 1H), 1.81 (dddd, J=20.2, 11.7, 7.1 Hz, 1H), 1.69-1.50 (m, 1H), 1.49-1.30 (m, 2H), 0.95 (t, J=7.3 Hz, 3H). MS (ESI): m/z 302.1 [M+H]$^+$. [α]$_D^{19}$ +67.0° (c=1.0 g/100 mL, CHCl$_3$).

Method II:

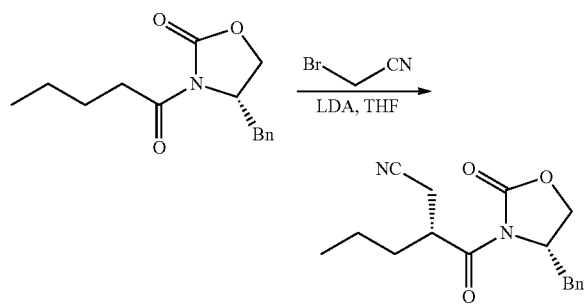

In a reaction flask, tetrahydrofuran (100.0 mL) was added, (S)-4-benzyl-3-pentanoyloxazol-2-one (10.0 g, 38.3 mmol) was added, and the temperature was cooled to −70° C.; under nitrogen gas protection, the internal temperature was maintained at −65~−75° C., 1.6 M solution of LDA in tetrahydrofuran (28.7 mL, 45.9 mmol, 1.2 eq) was added dropwise, after the addition, the reaction was conducted for 1 hour at a maintained temperature; then the internal temperature was maintained at −65~−75° C., bromoacetonitrile (6.9 g, 57.5 mmol, 1.5 eq) was added dropwise, and the reaction conducted for 1-2 hours at a maintained temperature. TLC was used to detect the disappearance of (S)-4-benzyl-3-pentanoyloxazol-2-one and treatment was performed; then the temperature was raised to 0° C., 200.0 mL saturated aqueous ammonium chloride solution was added to separate the phase. The organic phase was concentrated under a reduced pressure to dryness. The concentrate was dissolved in 100.00 mL methylene dichloride, washed with water twice (50.0 mL×2). The organic phase was dried over 30.0 g anhydrous sodium sulfate for 2 hours; filtered and concentrated under a reduced pressure to give 12.0 g crude product. Then 22.0 mL of ethanol was added to the crude product, heated to reflux, dissolved and crystallized after cooled, when cooled to 0~5°, stirred for 1 hour at a constant temperature, filtered and the filter cake was rinsed with a small amount of ethanol, after rinsed, the solid was dried in a vacuum oven for 4 hours to give the target product as a white solid (9.8 g, yield 85.2%).

Embodiment 5: Synthesis of (R)-3-((S)-4-phenyl-2-oxooxazolyl-3-carbonyl) hexanenitrile

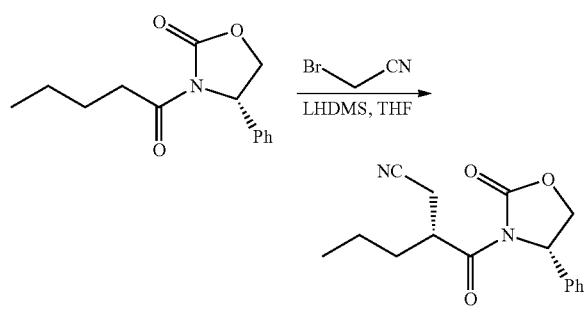

In a reaction flask, tetrahydrofuran (50.0 mL) was added, (S)-4-phenyl-3-pentanoyloxazol-2-one (5.0 g, 20.2 mmol) was added, and the temperature was cooled to −70° C.; under nitrogen gas protection, the internal temperature was maintained at −65~−75° C., 1.0M solution of LHMDS in tetrahydrofuran (24.3 mL, 24.3 mmol, 1.2 eq) was added dropwise, after the addition, the reaction was conducted for an hour at a maintained temperature; then the internal temperature was maintained at −65~−75° C., bromoacetonitrile (3.6 g, 30.0 mmol, 1.49 eq) was added dropwise, after the addition, the reaction was conducted for 1-2 hours at a maintained temperature, and TLC was used to detect the disappearance of (S)-4-phenyl-3-pentanoyloxazol-2-one, and treatment was performed; then the temperature was raised to 0° C., 25.0 mL saturated aqueous ammonium chloride solution was added to separate the phase. The organic phase was concentrated under a reduced pressure to dryness. The concentrate was dissolved in 50.0 mL methylene dichloride, washed with water twice (25.0 mL×2). The organic phase was dried over 10.0 g anhydrous sodium sulfate for 2 hours; filtered and concentrated under a reduced pressure to give the target product as a light yellow solid (5.6 g, yield 96.7%).

$^1$H NMR (600 MHz, CDCl$_3$) δ 7.40 (ddd, J=9.0, 7.3, 1.5 Hz, 2H), 7.37-7.33 (m, 1H), 7.32-7.28 (m, 2H), 5.42 (dt, J=9.1, 2.7 Hz, 1H), 4.72 (tt, J=8.8, 1.3 Hz, 1H), 4.35-4.27 (m, 1H), 4.15 (p, J=7.5 Hz, 1H), 2.57 (ddt, J=16.8, 7.4, 1.2 Hz, 1H), 2.49 (ddt, J=16.8, 6.0, 1.2 Hz, 1H), 1.79 (tdd, J=15.0, 6.3, 1.6 Hz, 1H), 1.66-1.56 (m, 1H), 1.45-1.32 (m, 2H), 0.95 (tt, J=7.3, 1.2 Hz, 3H). MS (ESI): m/z 287.1 [M+H]$^+$. [α]$_D^{19}$ +87.0° (c=1.0 g/100 mL, CHCl$_3$).

Embodiment 6: Synthesis of (R)-3-((S)-4-isopropyl-2-oxooxazolidinyl-3-carbonyl) hexanenitrile

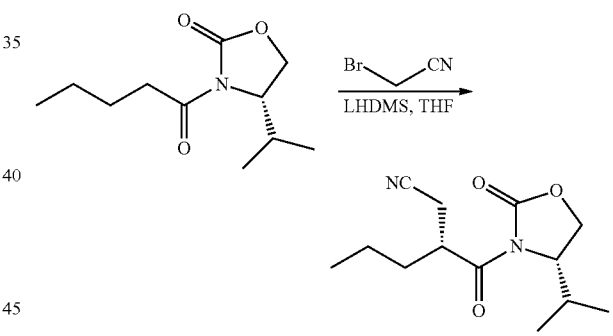

In a reaction flask, tetrahydrofuran (50.0 mL) was added, (S)-4-isopropyl-3-pentanoyloxazol-2-one (5.0 g, 23.4 mmol) was added, and the temperature was cooled to −70° C.; under nitrogen gas protection, the internal temperature was maintained at −65~−75° C., 1.0M solution of LHMDS in tetrahydrofuran (28.1 mL, 28.1 mmol, 1.2 eq) was added dropwise, after the addition, the reaction was conducted for an hour at a maintained temperature; then the internal temperature was maintained at −65~−75° C., bromoacetonitrile (4.2 g, 35.0 mmol, 1.5 eq) was added dropwise, after the addition, the reaction was conducted for 1-2 hours at a maintained temperature, and TLC was used to detect the disappearance of (S)-4-isopropyl-3-pentanoyloxazol-2-one, and treatment was performed; then the temperature was raised to 0° C., 25.0 mL saturated aqueous ammonium chloride solution was added to separate the phase. The organic phase was concentrated under a reduced pressure to dryness. The concentrate was dissolved in 50.0 mL methylene dichloride, washed with water twice (25.0 mL×2). The organic phase was dried over 10.0 g anhydrous sodium sulfate for 2 hours; filtered and concentrated under a reduced pressure to give the target product as a light yellow oily substance (5.8 g, yield 98.3%).

¹H NMR (600 MHz, CDCl₃) δ 4.46 (ddd, J=8.3, 3.8, 2.9 Hz, 1H), 4.31 (dd, J=9.2, 8.2 Hz, 1H), 4.25 (dd, J=9.2, 3.0 Hz, 1H), 4.15 (dtd, J=7.7, 6.7, 5.5 Hz, 1H), 2.71 (dd, J=16.7, 7.9 Hz, 1H), 2.60 (dd, J=16.7, 5.4 Hz, 1H), 2.43 (pd, J=7.0, 3.8 Hz, 1H), 1.78 (ddt, J=13.6, 10.0, 6.2 Hz, 1H), 1.63-1.51 (m, 1H), 1.44-1.29 (m, 2H), 0.99-0.86 (m, 9H). MS (ESI): m/z 275.1 [M+Na]⁺. [α]$_D^{19}$ +74.0° (c=1.0 g/100 mL, CHCl₃).

Embodiment 7: Synthesis of (R-3-(hydroxymethyl)hexanenitrile

Method I:

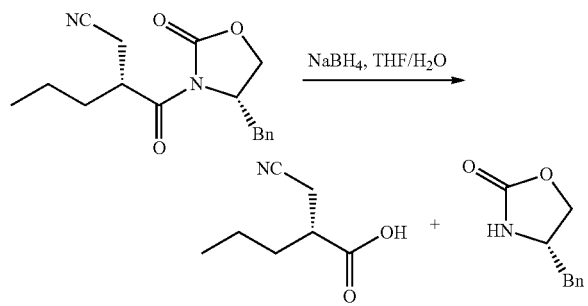

In a reaction flask, tetrahydrofuran (16.0 mL) and water (4.0 mL) were added, then (R)-3-((S)-4-benzyl-2-oxooxazolidinyl-3-carbonyl)hexanenitrile (2.4 g, 8.0 mmol) was added, maintaining the internal temperature below 40° C., and then sodium borohydride (0.60 g, 15.86 mmol, 1.98 eq) was added portionwise. The reaction was conducted at room temperature for 2 hours, and TLC was used to detect the disappearance of (R)-3-((S)-4-benzyl-2-oxooxazolidinyl-3-carbonyl) hexanenitrile and treatment was performed; when the internal temperature was controlled below 40° C., saturated ammonium chloride (12.0 mL) was added dropwise, and then the solution was separated, the aqueous phase was extracted with methyl t-butyl ether (10.0 mL), and the organic phase was combined and concentrated under reduced pressure at 40° C. to dryness. Methyl tert-butyl ether/n-hexane (2.4 mL, 2:1, v/v) was added to the concentrate, cooled to 0-10° C. and the mixture was stirred for 1 hour, filtered and (S)-4-benzoyloxazole-2-one was recovered, to give the product as white powder (1.05 g). The mother liquor was concentrated to dryness, and after purification by column chromatography, the target compound was given as a colorless oily substance (0.91 g, yield 89.2%).

¹H NMR (400 MHz, CDCl₃) δ 3.72 (dd, J=10.8, 4.4 Hz, 1H), 3.55 (dd, J=10.8, 7.5 Hz, 1H), 2.49 (d, J=5.8 Hz, 2H), 2.01 (s, 1H), 1.97-1.85 (m, 1H), 1.51-1.30 (m, 4H), 0.94 (dd, J=9.5, 4.0 Hz, 3H). MS (ESI): m/z 128.2 [M+H]⁺. [α]$_D^{19}$ +13.5° (c=1.0 g/100 mL, MeOH).

Method II:

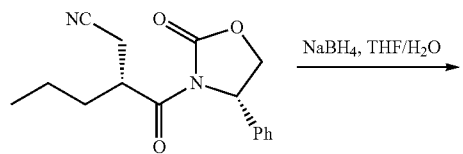

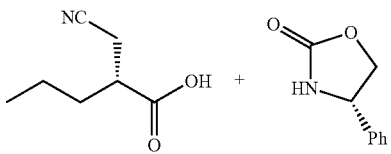

In a reaction flask, tetrahydrofuran (8.0 mL) and water (2.0 mL) were added, then (R)-3-((S)-4-phenyl-2-oxooxazolidinyl-3-carbonyl) hexanenitrile (1.20 g, 4.85 mmol) was added, maintaining the internal temperature below 40° C., and then sodium borohydride (0.37 g, 9.78 mmol, 2.0 eq) was added portionwise. The reaction was conducted at room temperature for 2 hours, and TLC was used to detect the disappearance of (R)-3-((S)-4-phenyl-2-oxooxazolidinyl-3-carbonyl) hexanenitrile and treatment was performed; when the internal temperature was controlled below 40° C., saturated ammonium chloride (6.0 mL) was added dropwise for quenching, then the mixture was distilled under reduced pressure at 40° C. until no fraction, and extracted with ethyl acetate (10.0 mL) to separate phases, the organic phase was dried over anhydrous sodium sulfate (2.0 g), filtered and the filtrate was concentrated under a reduced pressure. After purification by column chromatography, the target compound was given as a colorless oily substance (0.57 g, yield 91.9%).

Method III:

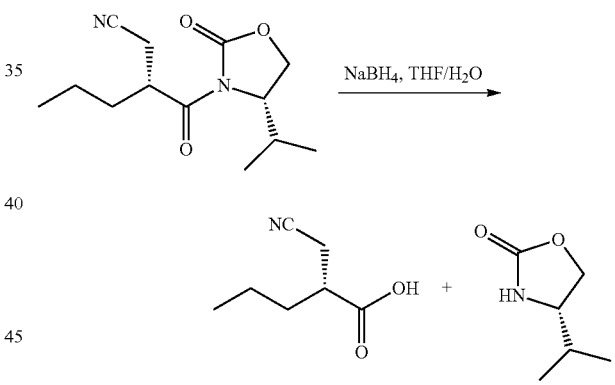

In a reaction flask, tetrahydrofuran (8.0 mL) and water (2.0 mL) were added, then (R)-3-((S)-4-isopropyl-2-oxooxazolidinyl-3-carbonyl)hexanenitrile (1.20 g, 4.76 mmol) was added, maintaining the internal temperature below 40° C., and then sodium borohydride (0.36 g, 9.52 mmol, 2.0 eq) was added portionwise. The reaction was conducted at room temperature for 2 hours, and TLC was used to detect the disappearance of starting materials and treatment was performed; when the internal temperature was controlled below 40° C., saturated ammonium chloride (6.0 mL) was added dropwise for quenching, then the mixture was distilled under reduced pressure at 40° C. until no fraction, and extracted with ethyl acetate (10.0 mL) to separate phases, the organic phase was dried over anhydrous sodium sulfate (2.0 g), filtered and the filtrate was concentrated under a reduced pressure. After purification by column chromatography, the target compound was given as a colorless oily substance (0.52 g, yield 86.7%).

Embodiment 8: Synthesis of (R)-4-n-propyl-dihydrofuran-2(3H)-one

Method I:

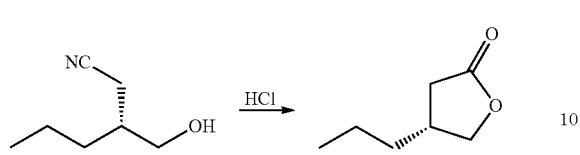

(R)-3-(hydroxymethyl)hexanenitrile (0.90 g) was added to 6N HCl (6.0 mL) aqueous solution, heated to 75±5° C. for reaction for 1 hour while stirring. TLC was used to detect the disappearance of the starting materials. The reaction was cooled to room temperature by stopping heating, and the mixture was extracted with methyl tert-butyl ether (10.0 mL×2), the organic phases were combined and washed once with water, and dried over anhydrous sodium sulfate (2.0 g), filtered and concentrated under a reduced pressure to give the target compound as a colorless oily substance (0.87 g, yield 95.6%).

$^1$H NMR (400 MHz, CDCl$_3$) δ4.42 (dd, J=8.9, 7.2 Hz, 1H), 3.92 (dd, J=8.9, 7.0 Hz, 1H), 2.68-2.50 (m, 2H), 2.18 (dd, J=16.6, 7.6 Hz, 1H), 1.46 (q, J=6.9 Hz, 2H), 1.36 (dqd, J=14.3, 7.3, 4.6 Hz, 2H), 0.94 (t, J=7.3 Hz, 3H). MS (EI, 70 eV): m/e (rel.inten.) 128 (M$^+$, 4), 110 (2), 97 (29), 70 (55), 69 (42), 56 (100), 55 (92). [α]$_D^{19}$ +6.88° (c=1.22 g/100 mL, CHCl$_3$).

Method II:

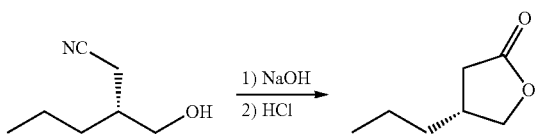

(R)-3-(hydroxymethyl)hexanenitrile (0.90 g) was added to tetrahydrofuran (2.0 mL) and 4N sodium hydroxide (8.0 mL), heated to 75±5° C. for reaction for 5 hours while stirring. TLC was used to detect the disappearance of the starting materials. The reaction was cooled to room temperature by stopping heating, and the organic phase was extracted with methyl tert-butyl ether (5.0 mL×2) and removed. Concentrated hydrochloric acid (15.0 mL) was added to the aqueous phase, and the mixture was heated to 40±5° C. for reaction for 1 hour while stirring. Then the reaction was stopped and cooled to room temperature, and the solution was extracted with methyl tert-butyl ether (5.0 mL×2), the organic phase was combined and washed with water once, dried over anhydrous sodium sulfate (2.0 g), filtered and concentrated under a reduced pressure to give the target compound as a colorless oily substance (0.85 g, yield 93.4%).

The invention claimed is:

1. A process for preparing optically pure (R)-4-n-propyl-dihydrofuran-2(3H)-one, comprising the following steps:
   1) preparing an optically pure (R)-3-(hydroxymethyl) hexanenitrile compound of formula (V);
   2) conducting cyano hydrolysis and lactonization of (R)-3-(hydroxymethyl)hexanenitrile compound of formula (V) under acidic conditions to obtain optically pure (R)-4-n-propyl-dihydrofuran-2(3H)-one of formula I, or conducting cyano hydrolysis, acidification and lactonization under alkaline conditions to obtain optically pure (R)-4-n-propyl-dihydrofuran-2(3H)-one of formula I;

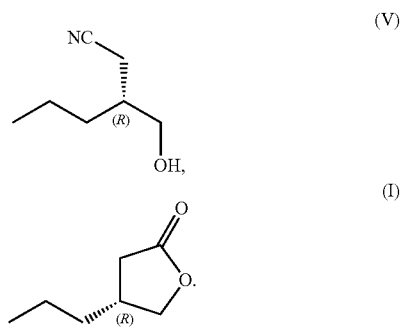

2. The preparation process according to claim 1, wherein the acid used for cyano hydrolysis or/and lactonization is an organic acid or an inorganic acid, and the organic acid is p-toluenesulfonic acid, trifluoroacetic acid, formic acid, acetic acid or propionic acid; the inorganic acid is hydrochloric acid, sulfuric acid, nitric acid or phosphoric acid.

3. The preparation process according to claim 2, wherein the acid used for cyano hydrolysis or/and lactonization is hydrochloric acid or sulfuric acid.

4. The preparation process according to claim 1, wherein the base used for cyano hydrolysis is sodium hydroxide, potassium hydroxide, lithium hydroxide, potassium carbonate or sodium carbonate.

5. The preparation process according to claim 4, wherein the base used for cyano hydrolysis is sodium hydroxide.

6. The preparation process according to claim 1, the reaction solvent of the cyano hydrolysis is water, or a mixed solvent of water and tetrahydrofuran, and the reaction temperature of cyano hydrolysis is 0~100° C.

7. The preparation process according to claim 6, wherein the reaction temperature for acid hydrolysis of cyano group is 80 to 100° C., and the reaction temperature for basic hydrolysis of cyano group is 70 to 90° C.

8. The preparation process according to claim 1, wherein for the method for preparing a compound of formula (V) in step (1), a compound of the formula (IV) is used to prepare an optically pure (R)-3-(hydroxymethyl) hexanenitrile compound of formula (V) in the presence of a reducing agent, and (S)-4-substituted oxazol-2-one of the formula VI as a prosthetic group is recycled

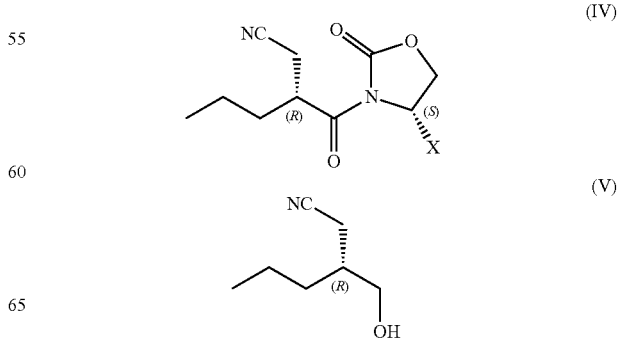

(VI)

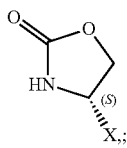

X is a $C_{1-20}$ alkyl, $C_{1-20}$ alkenyl, aryl, heteroaryl, heterocycloalkyl, arylalkyl or heteroarylalkyl.

9. The preparation process according to claim 8, wherein is methyl, ethyl, n-propyl, isopropyl, tert-butyl, benzyl, substituted benzyl, phenyl or substituted phenyl.

10. The preparation process according to claim 9, wherein X is phenyl, isopropyl or benzyl.

11. The preparation process according to claim 8, wherein the reducing agent is lithium borohydride, sodium borohydride, potassium borohydride, L-selectride or K-selectride.

12. The preparation process according to claim 11, wherein the reaction solvent for the reduction of the compound of formula (IV) is one or more of water, tetrahydrofuran, methanol, ethanol, isopropanol, and the reaction temperature is 0 to 100° C., the molar ratio of the compound of formula (IV) to the reducing agent is 1:0.5-5.

13. The preparation process according to claim 12, wherein the reaction solvent for the reduction of the compound of formula (IV) is a mixed solvent of water/tetrahydrofuran, water/methanol, water/ethanol, and the molar ratio of the compound of formula (IV) to the reducing agent is 1:1.0-2.0.

14. The preparation process according to claim 8, wherein the method for preparing the compound of formula (IV) comprises the following steps:
A) providing the compound of optically pure (S)-3-n-pentanoyl-4-substituted oxazol-2-one of formula (II),
B) carrying out an alkyl group substitution reaction between the compound of formula (II) and substituted acetonitrile of formula (III) in the presence of an alkaline reagent to generate a compound of formula (IV), (II)

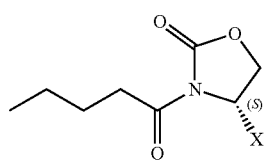

(III)

NC—Y (IV)

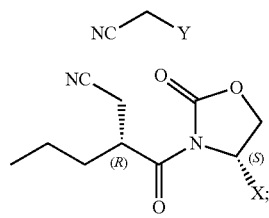

where,
Y is a leaving group selected from the group consisting of a halogen, a sulfonate group, —S$^{30}$(CH$_3$)$_2$ and —N$_2^{30}$ leaving group.

15. Preparation process according to claim 14, wherein the base used for the alkylation is lithium diisopropylamide, lithium hexamethyldisilazide, potassium hexamethyldisilazide and sodium hexamethyldisilazide.

16. The preparation process according to claim 15, wherein the reaction solvent for alkylation is tetrahydrofuran or 2-methyltetrahydrofuran, and the reaction temperature for alkylation is 20 to −80° C., the molar ratio of the compound of formula (II) to the compound of formula (III) is 1:0.9-5 and the molar ratio of the compound of formula (II) to the base is 1:0.9-3.

17. The preparation process according to claim 16, wherein the reaction temperature for alkylation is −60 to −75° C., the molar ratio of the compound of formula (II) to the compound of 1:1.0-1.5.

18. The preparation process according to claim 14, wherein the Y is fluorine, chlorine, bromine, iodine, methanesulfonyloxy, trifluoromethanesulfonyloxy or p-toluenesulfonyloxy.

19. The preparation process according to claim 18, wherein the Y is bromine.

20. The preparation process according to claim 14, wherein X is a benzyl group, the solvent for recrystallization of the compound of formula (IV) is selected from the group consisting of methanol, ethanol, isopropanol, methyl tert-butyl ether, acetone, butanone, isopropyl ether, n-heptane/ethyl acetate, methanol/water, ethanol/water, isopropanol/water, and acetonitrile/water.

21. The preparation process according to claim 20, wherein X is a benzyl group, and the solvent for recrystallization of the compound of formula (IV) is ethanol or isopropanol.

* * * * *